United States Patent
Yamamoto et al.

(10) Patent No.: US 7,645,599 B2
(45) Date of Patent: Jan. 12, 2010

(54) METHODS FOR PRODUCING OPTICALLY ACTIVE ALCOHOLS

(75) Inventors: Hiroaki Yamamoto, Ibaraki (JP); Momoko Ueda, Ibaraki (JP); Ritsuzui Pan, Niigata (JP); Takeshi Hamatani, Niigata (JP)

(73) Assignee: Daicel Chemical Industries, Ltd., Osaka (JP)

( * ) Notice: Subject to any disclaimer, the term of this patent is extended or adjusted under 35 U.S.C. 154(b) by 102 days.

(21) Appl. No.: 11/151,764

(22) Filed: Jun. 13, 2005

(65) Prior Publication Data

US 2005/0227336 A1    Oct. 13, 2005

Related U.S. Application Data

(62) Division of application No. 10/314,394, filed on Dec. 6, 2002, now abandoned.

(60) Provisional application No. 60/385,434, filed on May 31, 2002.

(30) Foreign Application Priority Data

Dec. 7, 2001 (JP) ............................ 2001-375041
May 27, 2002 (JP) ............................ 2002-152955

(51) Int. Cl.
*C12N 7/02* (2006.01)
*C12N 9/04* (2006.01)
*C12Q 1/00* (2006.01)
*C12Q 1/68* (2006.01)
*C12N 1/20* (2006.01)
*C12N 15/00* (2006.01)
*C07H 21/04* (2006.01)
*C12Q 21/04* (2006.01)
*C12Q 1/32* (2006.01)

(52) U.S. Cl. .......................... 435/155; 435/190; 435/4; 435/6; 435/26; 435/252.3; 435/320.1; 435/440; 435/69.1; 453/71.1; 536/23.2

(58) Field of Classification Search .................. None
See application file for complete search history.

(56) References Cited

U.S. PATENT DOCUMENTS

| | | | |
|---|---|---|---|
| 5,215,918 A | 6/1993 | Muchmore | |
| 5,744,606 A | 4/1998 | Brieden | |
| 5,888,804 A * | 3/1999 | Matsuyama et al. | 435/280 |
| 6,121,025 A | 9/2000 | Sato | |

FOREIGN PATENT DOCUMENTS

| CA | 2194727 | | 4/2005 |
|---|---|---|---|
| DE | 19715465 A1 | | 9/1997 |
| DE | 19715564 A1 | | 9/1997 |
| EP | 577253 A2 | | 1/1994 |
| EP | 577253 A3 | | 1/1994 |
| EP | 945518 A1 | | 9/1997 |
| EP | 863212 A2 | | 9/1998 |
| EP | 863212 A3 | | 9/1998 |
| EP | 955375 A2 | | 11/1999 |
| EP | 955375 A3 | | 11/1999 |
| EP | 1013758 A2 | | 6/2000 |
| EP | 1013758 A3 | | 6/2000 |
| JP | 05-194509 | | 8/1993 |
| JP | 05-194510 | | 8/1993 |
| JP | 6-56830 | | 3/1994 |
| JP | 9-194480 | | 7/1997 |
| JP | 10-210997 | | 8/1998 |
| JP | 10-243795 A | | 9/1998 |
| JP | 11-196890 A | | 7/1999 |
| JP | 2000-189170 | | 7/2000 |
| JP | 2000-236883 | | 9/2000 |
| JP | 2000-245495 | | 9/2000 |
| JP | 3129663 | | 11/2000 |
| JP | 2002-153293 | | 5/2002 |
| WO | WO 01/61014 A1 | | 8/2001 |

OTHER PUBLICATIONS

Branden et al. Introduction to Protein Structure, Garland Publishing Inc., New York, p. 247, 1991).*
Wong et al. Enzymatic v. Fermentative Synthesis: Thermostable Glucose Dehydrogenase Catalyzed Regeneration of NAD(P)H for use in Enzymatic SynthesiJ. Am. Chem. Soc., 1985, 107 (13), pp. 4028-4031.*
Kalir, A., et al., "Preparation of (+)-3-Quinuclidinol," *Israel Journal of Chemistry*, vol. 9:267-268 (1971).
Rehavi, Moshe, et al., "Enzymatic Resolution and Cholinergic Properties of (±)3-Quinuclidinol Derivatives," *Life Sciences*, vol. 21:1293-1302 (1977).
Boswell, et al. "Specificities of the enzymes of N-alkyltropane biosynthesis in *Brugmansia* and *Datura*." *Phytochemistry*. Nov. 1999;52(5):871-8.
Bright et al. "Cloning, sequencing and expression of the gene encoding glucose dehydrogenase from the thermophilic archaeon *Thermoplasma acidophilum*." *Eur. J. Biochem.* Feb. 1, 1993;211(3):549-54.

(Continued)

*Primary Examiner*—Yong D Pak
(74) *Attorney, Agent, or Firm*—Lahive & Cockfield, LLP; Jeanne M. DiGiorgi, Esq.; Maneesh Gulati, Esq.

(57) ABSTRACT

A method for producing optically active alcohols is provided. Optically active alcohols are useful intermediates in pharmaceutical production. The method of the present invention enables simple and efficient production of optically active alcohols with a high optical purity. According to the production method disclosed, optically active alcohols are produced via asymmetric reduction of 3-quinuclidinone using tropinone reductase-I. For example, the use of tropinone reductase-I derived from plants like *Datura stramonium* and *Hyoscyamus niger* allows the production of high optical purity (R)-3-quinuclidinol.

10 Claims, No Drawings

OTHER PUBLICATIONS

Cheronis, N.D. "Semimicro experimental organic chemistry." 1958 De Greff Pub. Ch. 5, pp. 31-43.

Hashimoto, T. et al. "Two tropinone reductases with distinct stereospecificities from cultured roots of *Hyoscyamus niger*[1]." *Plant Physiol.* 1992 100:836-45.

Koelen et al. "Partial purification and properties of tropine dehydrogenase from root cultures of *Datura stramonium*." *Planta Medica* 1982;44(4):227-30.

Nakajima, K. et al "Two tropinone reductases with different stereospecificities are short-chain dehydrogenases evolved from a common ancestor." *Proc. Natl. Acad. Sci. USA* Oct. 1993;90:9591-95.

Nakajima, K. et al. "Opposite stereospecificity of two tropinone reductases in conferred by the substrate-binding sites." *J. Biol. Chem.* Apr. 22, 1994;269(16):11695-8.

Nakajima et al. "Site-directed mutagenesis of putative substrate-binding residues reveals a mechanism controlling the different stereospecificities of two tropinone reductases." *J. Biol. Chem.* Jun. 4, 1999;274(23):16563-8.

Nakajima et al. "Insight into the molecular evolution of two tropinone reductases." *Biosci.. Biotechnol. Biochem.* Oct. 1999;63(10):1819-22.

Nakajima et al. "Structures and expression patterns of two tropinone reductase genes form *Hyoscyamus niger*." *Biosci. Biotechnol. Biochem.* Oct. 1999;63(10):1756-64.

Portseffen, A. et al. "The reduction of tropinone in *Datura stramonium* root cultures by two specific reductases." *Phytochemistry* 1994 37(2):391-400.

Pyttel, R. *J. Pharm. Sci.* "Interaction of 3-quinuclidinol and its derivatives with acetylcholinesterase." Apr. 1973;62(4)684-5.

\* cited by examiner

METHODS FOR PRODUCING OPTICALLY ACTIVE ALCOHOLS

RELATED APPLICATIONS

This application is a division of U.S. patent application Ser. No. 10/314,394, entitled "Methods for Producing Optically Active Alcohols", filed on Dec. 6, 2002, now abandoned, which claims priority to Japanese Patent Application Serial No. 2001-375041 filed on Dec. 7, 2001, Japanese Patent Application Serial No. 2002-152955 filed on May 27, 2002, and U.S. Provisional Patent Application Ser. No. 60/385,434 filed on May 31, 2002. The entire contents of each application is hereby expressly incorporated herein by reference.

FIELD OF THE INVENTION

The present invention relates to methods for producing optically active alcohols using tropinone reductase-I.

BACKGROUND OF THE INVENTION

Optically active alcohols are useful as an asymmetric source for synthesizing various optically active compounds. Typically, optically active alcohols are produced through optical resolution of racemates or asymmetric synthesis. In particular, the technology for optically active alcohol production through asymmetric synthesis is recognized to be essential to produce optically active alcohols on a large scale.

(R)-3-quinuclidinol is an industrially useful optically active alcohol. Optically active (R)-3-quinuclidinol has been used as an important intermediate to produce a variety of physiologically active or pharmacological active agents, for example, in therapeutic agents for arteriosclerosis, which have the activity of inhibiting squalene synthase, bronchodilators having antagonistic action to the muscarinic receptor, agents suppressing gastrointestinal motility, etc. (Unexamined Published Japanese Patent Application No. (JP-A) Hei 8-134067; EP-404737A2; EP-424021A1; WO92/04346; and WO93/06098).

So far known methods for producing optically active 3-quinuclidinol include, a method where the compound is produced through optical resolution of the acetylated form of 3-quinuclidinol racemate with tartaric acid, followed by hydrolysis (Acta Pharm. Suec. 16(4), 281-3 (1979)).

Another known production method using a microorganism or enzyme comprises selective asymmetric hydrolysis of (S)-3-quinuclidinol ester by allowing one of the microorganisms or enzymes described below to react to the racemate of 3-quinuclidinol ester that is a raw material, and the subsequent hydrolysis of residual (R)-3-quinuclidinol ester.

Subtilisin protease (U.S. Pat. No. 5,215,918);

Esterases derived from the genus *Aspergillus* or the genus *Pseudomonas* (JP-A Hei 10-210997); and Cells of microorganisms belonging to the genus *Aspergillus*, the genus *Rhizopus*, the genus *Candida*, and the genus *Pseudomonas* (JP-A Hei 10-136995), and enzymes derived therefrom.

In addition, an alternative production method has been reported, which comprises selective asymmetric hydrolysis of (R)-3-quinuclidinol ester by contacting horse serum esterase with the racemate of 3-quinuclidinol ester that is a raw material (Life Sci. 21(9), 1593-302 (1977)). Further, there is another known method where, using the racemate of 3-quinuclidinol as a raw material, the R form is obtained by converting, with subtilisin protease, only the S form to (S)-3-quinuclidinyl butyrate (German Patent No. 19715465).

However, the product obtained by these production methods has only low optical purity. In addition, these production methods have complicated synthesis steps. Thus, any of the methods described above cannot be said as the methods for simply and economically producing (R)-3-quinuclidinol.

Additional known methods for producing optically active 3-quinuclidinol from 3-quinuclidinone, comprises asymmetric reduction using microorganisms or enzymes (JP-A Hei 10-243795; JP-A Hei 11-196890; JP-A 2000-245495; Abstract (2001) The Japan Agricultural Chemical Society, pp. 371 3Y7a9). In this reaction, the optically active compound is produced directly by incubating a substrate compound with a wild-type microorganism. The reaction consists of a single reaction step, thus the method has greatly been simplified. However, there still remain some problems; the optical purity of the product is low and the concentration of the product obtained is also low.

SUMMARY OF THE INVENTION

An objective of the present invention is to provide a method for efficiently producing optically active alcohols with high optical purity using tropinone reductase-I.

The present inventors focused on the reducing action of ketone reductase for economic and convenient production of optically active alcohols. They found that optically active alcohols with high optical purity can be efficiently produced by using the reducing action of tropinone reductase-I, which is a ketone reductase, and thus completed the present invention.

Furthermore, in order to improve the efficiency of production of optically active alcohols by using tropinone reductase-I, the present inventors studied the usefulness of co-expression of tropinone reductase-I and an enzyme that is capable of regenerating a coenzyme from its oxidized form generated via asymmetric reduction. Then, they found that the co-expression of the two enzymes enabled more efficient production of optically active alcohols. They found that, particularly, co-expression of tropinone reductase-I and a specific glucose dehydrogenase achieved extremely high efficiency of synthesis. Thus, the present invention relates to the methods for producing optically active alcohols; vectors, which are used in the production method, for co-expressing a ketone reductase and an enzyme responsible for regeneration of a coenzyme from the oxidized form; and transformants carrying the vectors. The present invention also relates to a method for crystallizing optically active alcohols obtained by the above-mentioned production method. These inventions are as follows:

[1] A method for producing an optically active alcohol, the method comprising the steps of contacting a ketone with an enzymatic material having tropinone reductase-I activity in the presence of a reduced coenzyme to perform asymmetric reduction and recovering an optically active alcohol.

[2] The method according to [1], wherein the ketone is 3-quinuclidinone and the optically active alcohol is (R)-3-quinuclidinol.

[3] The method according to [1], wherein the enzymatic material has tropinone reductase-I activity to produce an optically active alcohol with 70% ee or higher optical purity.

[4] The method according to [1], wherein the enzymatic material is derived from a plant belonging to the genus *Datura* or the genus *Hyoscyamus*.

[5] The method according to [4], wherein the plant belonging to the genus *Datura* is *Datura stramonium*.

[6] The method according to [4], wherein the plant belonging to the genus *Hyoscyamus* is *Hyoscyamus niger*.

[7] The method according to [1], wherein the enzymatic material comprises a protein selected from the group consisting of (a) to (d):

(a) a protein comprising the amino acid sequence of SEQ ID NO: 2 or SEQ ID NO: 4;

(b) a protein comprising the amino acid sequence of SEQ ID NO: 2 or SEQ ID NO: 4 wherein one or more amino acids have been substituted, deleted, inserted, and/or added, and having the activity of producing (R)-3-quinuclidinol from 3-quinuclidinone by asymmetric reduction;

(c) a protein comprising an amino acid sequence having 85% or higher identity to the amino acid sequence of SEQ ID NO: 2 or SEQ ID NO: 4, and having the activity of producing (R)-3-quinuclidinol from 3-quinuclidinone by asymmetric reduction; and (d) a protein encoded by a polynucleotide capable of hybridizing to the polynucleotide comprising the nucleotide sequence of SEQ ID NO: 1 or SEQ ID NO: 3 under a stringent condition, and having the activity of producing (R)-3-quinuclidinol from 3-quinuclidinone by asymmetric reduction.

[8] The method according to [1], wherein the enzymatic material is a transformant carrying a DNA encoding tropinone reductase-I or a vector comprising a DNA encoding tropinone reductase-I, or a processed product of the transformant.

[9] The method according to [8], wherein the vector comprising the DNA selected from the group consisting of (a) to (d):

(a) a DNA comprising the nucleotide sequence of SEQ ID NO: 1 or SEQ ID NO: 3;

(b) a DNA that encodes a protein comprising the amino acid sequence of SEQ ID NO: 2 or SEQ ID NO: 4 wherein one or more amino acids have been substituted, deleted, inserted, and/or added and having the activity of producing (R)-3-quinuclidinol from 3-quinuclidinone by asymmetric reduction;

(c) a DNA comprising a nucleotide sequence having 85% or higher identity to the nucleotide sequence of SEQ ID NO: 1 or SEQ ID NO: 3, and encoding a protein having the activity of producing (R)-3-quinuclidinol from 3-quinuclidinone by asymmetric reduction; and (d) a DNA that is capable of hybridizing to a polynucleotide comprising the nucleotide sequence of SEQ ID NO: 1 or SEQ ID NO: 3 under a stringent condition, and encodes a protein having the activity of producing (R)-3-quinuclidinol from 3-quinuclidinone by asymmetric reduction.

[10] The method according to [8], wherein the vector further comprises a DNA encoding an enzyme of regenerating a reduced coenzyme from the oxidized form.

[11] The method according to [8], wherein the transformant further comprises a DNA encoding an enzyme of regenerating a reduced coenzyme from the oxidized form or a vector comprising a DNA encoding an enzyme of regenerating a reduced coenzyme from the oxidized form.

[12] The method according to [1], wherein the reduced coenzyme is NADPH or NADH.

[13] The method according to [10], wherein the enzyme of regenerating a reduced coenzyme from the oxidized form is selected from the group consisting of glucose dehydrogenase, glutamate dehydrogenase, formate dehydrogenase, malate dehydrogenase, glucose-6-phosphate dehydrogenase, phosphogluconate dehydrogenase, alcohol dehydrogenase, and glycerol dehydrogenase.

[14] The method according to [13], wherein the enzyme of regenerating a reduced coenzyme from the oxidized form is a glucose dehydrogenase.

[15] The method according to [14], wherein the glucose dehydrogenase is derived from *Bacillus subtilis* or *Thermoplasma acidophilum*.

[16] The method according to [1], wherein the asymmetric reduction is preformed at pH 6.5 to 8.5.

[17] A method for producing (R)-3-quinuclidinol hydrochloride, the method comprising the steps of:

(a) making the pH of (R)-3-quinuclidinol solution alkaline to form free (R)-3-quinuclidinol;

(b) extracting free (R)-3-quinuclidinol with n-butanol;

(c) adding hydrochloric acid to the extract;

(d) removing moisture from the extract; and (e) crystallizing (R)-3-quinuclidinol hydrochloride in the solution obtained in (d).

[18] A method for producing (R)-3-quinuclidinol, the method comprising the steps of:

(a) dissolving (R)-3-quinuclidinol hydrochloride in a first solvent, wherein the first solvent is capable of dissolving (R)-3-quinuclidinol hydrochloride at a concentration of 1% or higher;

(b) making the pH of the solution obtained in (a) alkaline to form free (R)-3-quinuclidinol;

(c) adding a second solvent to the (R)-3-quinuclidinol solution, wherein the second solvent can be substituted for the first solvent by distilling off the first solvent from a mixture of the first and second solvents, dissolves free (R)-3-quinuclidinol with lower solubility than the first solvent, and allows to crystallize free (R)-3-quinuclidinol from itself;

(d) distilling off the first solvent; and (e) crystallizing (R)-3-quinuclidinol in the solution obtained in (d).

[19] The method according to [18], wherein the second solvent is selected from the group consisting of toluene, hexane, 4-methyl-2-pentanone, and butyl acetate.

[20] The method according to [18], wherein the first solvent is water, and the second solvent is toluene.

[21] A method for producing (R)-3-quinuclidinol, the method comprising the steps of:

(a) making the pH of (R)-3-quinuclidinol solution alkaline to form free (R)-3-quinuclidinol;

(b) extracting free (R)-3-quinuclidinol with n-butanol; and (c) adding an organic solvent to the extract, wherein the organic solvent can be substituted for n-butanol by distilling off n-butanol from a mixture of n-butanol and the organic solvent, dissolves free (R)-3-quinuclidinol with lower solubility than n-butanol, and allows to crystallize free (R)-3-quinuclidinol from itself;

(d) distilling off n-butanol; and (e) crystallizing (R)-3-quinuclidinol in the solution obtained in (d).

[22] The method according to [21], wherein the organic solvent is selected from the group consisting of toluene, 4-methyl-2-pentanone, and butyl acetate.

[23] A vector comprising and capable of expressing a DNA encoding tropinone reductase-I and a DNA encoding an enzyme of regenerating a reduced coenzyme from the oxidized form.

[24] The vector according to [23], wherein the DNA encoding tropinone reductase-I is a DNA selected from the group consisting of (a) to (d):

(a) a DNA comprising the nucleotide sequence of SEQ ID NO: 1 or SEQ ID NO: 3;

(b) a DNA encoding a protein comprising the amino acid sequence of SEQ ID NO: 2 or SEQ ID NO: 4 wherein one or more amino acids have been substituted, deleted, inserted, and/or added and having an activity of producing (R)-3-quinuclidinol from 3-quinuclidinone by asymmetric reduction;

(c) a DNA comprising a nucleotide sequence having 85% or higher identity to the nucleotide sequence of SEQ ID NO: 1 or SEQ ID NO: 3, and encoding a protein having an activity of producing (R)-3-quinuclidinol from 3-quinuclidinone by asymmetric reduction; and (d) a DNA capable of hybridizing to a polynucleotide comprising the nucleotide sequence of SEQ ID NO: 1 or SEQ ID NO: 3 under a stringent condition, and encoding a protein having the activity of producing (R)-3-quinuclidinol from 3-quinuclidinone by asymmetric reduction.

[25] The vector according to [23], wherein the reduced coenzyme is NADPH or NADH.

[26] The vector according to [23], wherein the enzyme of regenerating a reduced coenzyme from the oxidized form is selected from the group consisting of glucose dehydrogenase, glutamate dehydrogenase, formate dehydrogenase, malate dehydrogenase, glucose-6-phosphate dehydrogenase, phosphogluconate dehydrogenase, alcohol dehydrogenase, and glycerol dehydrogenase.

[27] The vector according to [23], wherein the enzyme of regenerating a reduced coenzyme from the oxidized form is a glucose dehydrogenase.

[28] The vector according to [27], wherein the glucose dehydrogenase is derived from *Bacillus subtilis* or *Thermoplasma acidophilum*.

[29] A transformant carrying and capable of expressing (1) a DNA encoding tropinone reductase-I or a vector comprising a DNA encoding tropinone reductase-I and (2) a DNA encoding an enzyme of regenerating a reduced coenzyme from the oxidized form or a vector comprising a DNA encoding an enzyme of regenerating a reduced coenzyme from the oxidized form.

[30] The transformant according to [29], wherein the transformant carries and is capable of expressing the vector according to [23].

[31] The transformant according to [29], wherein a host is *Escherichia coli*.

DETAILED DESCRIPTION OF THE INVENTION

In one aspect, the present invention relates to a method for producing an optically active alcohol, the method comprising the step of contacting a ketone with an enzymatic material having tropinone reductase-I activity in the presence of a reduced coenzyme to perform asymmetric reduction and recovering an optically active alcohol produced.

An arbitrary enzymatic material can be used in the present invention as long as it has tropinone reductase-I activity and can produce optically active alcohols via asymmetric reduction of ketones.

As used herein, "tropinone reductase-I activity" means the activity of producing tropine from tropinone. There are reportedly two types of tropinone reductases, tropinone reductase-I (EC.1.1.1.206) and tropinone reductase-II (EC1.1.1.236), each of which produces tropine or pseudotropine from tropinone, which product has optically isomeric configurations. These enzymes catalyze the reaction at a branch point of the biosynthesis pathway of tropane alkaloids such as hyoscyamine and scopolamine. One of the tropinone reductases, tropinone reductase-I, derived from any of the following organisms, has been reported to exhibit the activity of reducing 3-quinuclidinone:

*Hyoscyamus niger* (Plant Physiol., 100, 836-845 (1992));
*Datura stramonium* (Phytochemistry, 37(2), 391-400 (1994));
*Brugmansia candida×aurea* hybrid (Phytochemistry, 52, 871-878 (1999)).

The tropinone reductase-II derived from *Brugmansia candida×aurea* hybrid has been reported to have the activity of reducing 3-quinuclidinone. The enzyme used in the present invention is tropinone reductase-I, which is the enzyme having the activity of producing tropine from tropinone.

The enzymatic activity of tropinone reductase-I can be assayed by, for example, incubating a reaction solution containing 100 mM potassium phosphate buffer (pH 6.5), 0.2 mM NADPH, 4 mM tropinone, and the enzyme at 37° C. and determining a decrease in the absorbance at 340 nm due to a decrease in a NADPH concentration. The 3-quinuclidinone-reducing activity can be determined by incubating a reaction solution containing 100 mM potassium phosphate buffer (pH 6.5), 0.2 mM NADPH, 4 mM 3-quinuclidinone, and the enzyme at 37° C. and determining a decrease in the absorbance at 340 nm due to a decrease in a NADPH concentration. In each case, one unit (U) is defined as an amount of the enzyme that catalyzes the decrease of 1 μmol NADPH for 1 minute.

As used herein, the term "optically active alcohol" means an alcohol in which the quantity of one optical isomer is larger than that of the other, or an alcohol comprising only one type of optical isomer. Furthermore, in some cases, "optical isomer" of the present invention generally refers to an "optically active form" or "enantiomer."

Thus, the enzyme capable of producing optically active alcohols via asymmetric reduction of ketones can be defined as an enzyme capable of producing an optically active alcohol corresponding to an arbitrary ketone compound given as a substrate.

There is no limitation on the origin of the enzymatic material to be used in the present invention. The preferred enzymatic material of the present invention can produce optically active alcohols with at least 70% ee or higher optical purity, preferably with 80% ee or higher optical purity when using a ketone as the substrate. The optical purity of the product can be determined by analyzing the reaction product using an optical resolution column or the like.

The preferred enzymatic material of the present invention is an enzyme that can be obtained, for example, from a plant species belonging to the genus *Datura* or the genus *Hyoscyamus*. Such enzymes are known, including tropinone reductase-I derived from *Datura stramonium* (Proc. Natl. Acad. Sci. U.S.A., 90, 9591-9595 (1993)) and tropinone reductase-I derived from *Hyoscyamus niger* (Biosci. Biotechnol. Biochem., 63(10), 1819-1822 (1999)).

Other tropinone reductase-I derived from various organisms can also be used, as long as it has the activity of producing optically active alcohols by reducing ketones. Other organisms from which tropinone reductase-I is derived include, *Brugmansia candida×aurea* hybrid (Phytochemistry, 52, 871-878 (1999)), *Atropa belladonna* (Plant Physiol., 100, 836-845 (1992)), *Physalis philadelphica* (Plant Physiol., 100, 836-845 (1992)), *Solanum tuberosum* (DNA Databank of JAPAN (DDBJ)), etc.

As described above, tropinone reductase-I is known to have ketone-reducing activity. It has been reported that the enzyme reduces 3-quinuclidinone and thus produces 3-quinuclidinol. However, the configuration and optical purity of 3-quinuclidinol produced have not been clarified. In addition, it is difficult to estimate the configuration of 3-quinuclidinol generated from 3-quinuclidinone based on the action on tropinone.

The present inventors strenuously studied the production of optically active alcohols via ketone reduction by tropinone reductase-I. They found that tropinone reductase-I produced optically active alcohols. Specifically, they found that, tropinone reductase-I enabled highly efficient production of (R)-3-quinuclidinol with high optical purity via asymmetric reduction of 3-quinuclidinone. They also clarified that the enzyme reaction can be used to produce optically active alcohols.

In the present invention, the enzymatic material includes enzymatic proteins, microorganisms, plants, plant cultured cells, and processed products of such organisms, having tropinone reductase-I activity.

The enzymatic proteins should be substantially pure. The term "substantially pure" as used herein in reference to a given protein means that the protein is substantially free from other biological macromolecules. The substantially pure protein is at least 75% (e.g., at least 80, 85, 95, or 99%) pure by dry weight. Purity can be measured by any appropriate standard method, for example by column chromatography, polyacrylamide gel electrophoresis, or HPLC analysis.

The enzymatic protein according to the present invention is preferably selected from the group consisting of:

(a) a protein comprising the amino acid sequence of SEQ ID NO: 2 or SEQ ID NO: 4;

(b) a protein comprising the amino acid sequence of SEQ ID NO: 2 or SEQ ID NO: 4 wherein one or more amino acids have been substituted, deleted, inserted, and/or added, and having the activity of producing (R)-3-quinuclidinol from 3-quinuclidinone by asymmetric reduction;

(c) a protein comprising an amino acid sequence having 85% or higher identity to the amino acid sequence of SEQ ID NO: 2 or SEQ ID NO: 4, and having the activity of producing (R)-3-quinuclidinol from 3-quinuclidinone by asymmetric reduction; and (d) a protein encoded by a polynucleotide capable of hybridizing to the polynucleotide comprising the nucleotide sequence of SEQ ID NO: 1 or SEQ ID NO: 3 under a stringent condition, and having the activity of producing (R)-3-quinuclidinol from 3-quinuclidinone by asymmetric reduction.

The microorganisms, plants, and plant cultured cells used in the present invention may be wild-type or transformants, containing and capable of expressing the gene encoding the above protein.

The processed product refers to a product obtained after physical treatment, biochemical treatment, chemical treatment, etc., of the above-described microorganisms, plants and plant cultured cells. The physical treatment for the processed product includes freeze-and-thaw treatment, sonication, pressurization, osmotic shock, and grinding. The biochemical treatment includes a treatment with a cell-lytic enzyme, specifically such as lysozyme. The chemical treatment includes a treatment with a detergent or an organic solvent such as toluene, xylene, or acetone. Specific examples of the processed product includes microorganisms whose cell membrane permeability has been altered by such a treatment, and cell-free extract yielded by crushing microbial or plant cells with glass beads or by enzyme treatment, and partially purified products. The purification can be performed by conventional methods including, filtration, centrifugation, precipitation, salting-out, extraction, and various chromatographic procedures such as ion-exchange chromatography, hydrophobic chromatography, affinity chromatography, and gel filtration, etc. These purification methods can be used alone or in combination of two or more.

The cells or the purified protein can be immobilized on a solid support. The method for immobilization is not particularly limited. The solid support includes, for example, glutaraldehyde, acrylamide, K-carrageenan, calcium alginate, ion-exchange resin, Celite, etc.

Purified enzymes that can be used as the enzymatic material can be isolated, from a plant such as *Datura stramonium* (Phytochemistry, 37(2), 391-400 (1994)) or *Hyoscyamus niger* (Plant Physiol., 100, 836-845 (1992)) via conventional methods well known in the art. Alternatively, transformants can be used as the enzymatic material. First, a gene encoding tropinone reductase-I is isolated. A transformant containing and capable of expressing the gene can be prepared by transforming a homologous or heterologous host with the gene by genetic recombination techniques. The transformant can be used as the enzymatic material without any modification or after processing as described above. Further, recombinant tropinone reductase-I obtained from the transformant by culturing the transformant in a culture medium and recovering the enzyme from the culture, can be used.

Known genes encoding tropinone reductase-I that can be used in the present invention include those from *Datura stramonium* and *Hyoscyamus niger*.

The nucleotide sequence of the tropinone reductase-I gene derived from *Datura stramonium* is shown in SEQ ID NO: 1 (Proc. Natl. Acad. Sci. U.S.A., 90, 9591-9595 (1993)), and the nucleotide sequence of the tropinone reductase-I gene derived from *Hyoscyamus niger* is shown in SEQ ID NO: 3 (Biosci. Biotechnol. Biochem., 63(10), 1819-1822 (1999)).

The nucleotide sequence information on these genes encoding tropinone reductase-I has been deposited in DNA databases such as DNA Databank of JAPAN (DDBJ), EMBL, Gene-Bank, etc. Based on the nucleotide sequence information, a gene of interest can be obtained from the source organism. PCR and hybridization screening can be used for preparing a gene. Alternatively, the full-length gene can be prepared chemically by DNA synthesis.

Moreover, based on the above nucleotide sequence information, it is possible to obtain tropinone reductase-I genes derived from other organisms in addition to the above-mentioned organisms. For example, tropinone reductase-I can be isolated from various organisms by hybridizing the above-mentioned nucleotide sequence or a partial sequence thereof as a probe to DNAs prepared from other organisms under stringent conditions. The polynucleotide capable of hybridizing under a stringent condition refers to a polynucleotide capable of hybridizing to a DNA comprising a nucleotide sequence selected from the nucleotide sequence of SEQ ID NO: 1 and SEQ ID NO: 3 as the probe, for example, by using ECL™ direct nucleic acid labeling and detection system (Amersham Pharmacia Biotech) under the condition as described in the manufacturer's instruction (wash: at 42° C. with a primary wash buffer containing 0.5×SSC). The nucleotide sequence of the probe DNA may comprise one or more sequences consisting of at least 20 consecutive residues, preferably at least 30 consecutive residues, for example, 40, 60, or 100 consecutive residues arbitrarily selected from the above-mentioned nucleotide sequence.

Furthermore, based on the above-mentioned nucleotide sequence information, PCR primers can be designed from regions exhibiting high homology. The gene encoding tropinone reductase-I can be isolated from various organisms by PCR using such primers and chromosomal DNA or cDNA as a template.

In the method of the present invention, it is possible to use not only the native enzyme but also a mutant enzyme comprising an amino acid sequence in which one or more amino acid residues have been substituted, deleted, and/or inserted as compared with the original amino acid sequence, so long as the mutant enzyme has the activity of producing (R)-3-quinuclidinol by reducing 3-quinuclidinone. Those skilled in the art can modify protein structures by introducing appropriate mutations of amino acid substitution, deletion, insertion, and/or addition, for example, by site-directed mutagenesis (Nucleic Acid Res. 10, pp. 6487 (1982); Methods in Enzymol. 100, pp. 448 (1983); Molecular Cloning 2nd Ed., Cold Spring Harbor Laboratory Press (1989); PCR A Practical Approach IRL Press pp. 200 (1991)) or the like. In the present invention, the number of amino acid residues that may be substituted, deleted, inserted, and/or added is, typically less than 50 residues, for example, less than 30 residues, or less than 20 residues, preferably less than 16 residues, more preferably less than 5 residues, still more preferably 0 to 3 residues. Amino acid mutations can be generated spontaneously, and therefore not only the enzymes containing artificial amino acid mutations but also the enzymes containing spontaneous mutations can be used in the method of the present invention.

An amino acid substitution is preferably mutated into different amino acid(s) in which the properties of the amino acid side-chain are conserved. A "conservative amino acid substitution," as employed in the present invention, refers to a replacement of one amino acid residue belonging to one of the following groups with similar side chain(s) with another amino acid from the same group. Groups of amino acid residues having similar side chains are well known to one of ordinary skill in the art. These groups include the following: amino acids with basic side chains (e.g., lysine, arginine, histidine); acidic side chains (e.g., aspartic acid, glutamic acid); uncharged polar side chains (e.g., glycine, asparagine, glutamine, serine, threonine, tyrosine, cysteine); nonpolar side chains (e.g., alanine, valine, leucine, isoleucine, proline, phenylalanine, methionine, tryptophan); beta-branched side chains (e.g., threonine, valine, isoleucine); and aromatic side chains (e.g., tyrosine, phenylalanine, tryptophan, histidine).

Furthermore, in the method of the present invention, a gene encoding a protein comprising an amino acid sequence having homology to that of tropinone reductase-I can also be used, as long as the enzyme as the gene product has the activity of producing (R)-3-quinuclidinol by reducing 3-quinuclidinone. Such genes can be obtained by homology search in the following databases.

Databases of protein amino acid sequences such as the SWISS-PRO™ database, the PIR™ database, etc.

DNA databases, such as DNA Databank of JAPAN (DDBJ)™ database, the EMBL™ database, the GeneBank™ database, etc.

Databases of deduced amino acid sequences based on DNA sequences

A number of known homology search programs such as FASTA and BLAST programs, can be used. Furthermore, services to search the above-mentioned databases by using these programs, are also available on the Internet. Using such services, it is possible to find tropinone reductase-I to be used in the present invention.

Proteins, which have at least 85% identity, preferably 90% or higher identity, more preferably 95% or higher identity to the amino acid sequence of SEQ ID NO: 2 (*Datura stramonium*) or SEQ ID NO: 4 (*Hyoscyamus niger*), can be used as preferred tropinone reductase-I in the present invention. Proteins comprising amino acid sequences of SEQ ID NO: 2 or SEQ ID NO: 4 were found to have enzymatic activity that can be used in the present invention. The identity between the two is 94%. The identity used herein means, for example, a "Positive" identity value obtained by using the BLAST program.

As used herein, "percent identity" of two amino acid sequences or of two nucleic acids is determined using the algorithm of Karlin and Altschul (Proc. Natl. Acad. Sci. USA 87: 2264-2268, 1990) modified as in Karlin and Altschul (Proc. Natl. Acad. Sci. USA 90:5873-5877, 1993). Such an algorithm is incorporated into the NBLAST and XBLAST programs of Altschul et al. (J. Mol. Biol. 215:403-410, 1990). BLAST nucleotide searches are performed with the NBLAST program, score=100, wordlength=12. Homology search of protein can readily be performed, for example, in DNA Databank of JAPAN (DDBJ), by using the FASTA program, BLAST program, etc. BLAST protein searches are performed with the XBLAST program, score=50, wordlength=3. Where gaps exist between two sequences, Gapped BLAST is utilized as described in Altsuchl et al. (Nucleic Acids Res. 25: 3389-3402, 1997). When utilizing BLAST and Gapped BLAST programs, the default parameters of the respective programs (e.g., XBLAST and NBLAST) are used.

Preferred enzymatic materials of the present invention include (i) transformants obtained by genetic recombination techniques that express the gene encoding tropinone reductase-I that has been introduced into a homologous or heterologous host; and (ii) processed product thereof.

In the present invention, there is no restriction on the organism to be transformed for expressing the gene encoding tropinone reductase-I, as long as the organism is capable of being transformed with the vector containing the DNA encoding the polypeptide with activity of tropinone reductase-I and capable of expressing activity of tropinone reductase-I. Available microorganisms are those for which host-vector systems are available and include the following examples:

bacteria such as the genus *Escherichia*, the genus *Bacillus*, the genus *Pseudomonas*, the genus *Serratia*, the genus *Brevibacterium*, the genus *Corynebacterium*, the genus *Streptococcus*, and the genus *Lactobacillus;* actinomycetes, such as, the genus *Rhodococcus* and the genus *Streptomyces;* yeasts such as the genus *Saccharomyces*, the genus *Kluyveromyces*, the genus *Schizosaccharomyces*, the genus *Zygosaccharomyces*, the genus *Yarrowia*, the genus *Trichosporon*, the genus *Rhodosporidium*, the genus *Pichia*, and the genus *Candida*; and fungi such as the genus *Neurospora*, the genus *Aspergillus*, the genus *Cephalosporium*, and the genus *Trichoderma*; etc.

Preparation of a Transformant and Construction of a Recombinant Vector Suitable for a host can be carried out by employing techniques that are commonly used in the fields of molecular biology, bioengineering, and genetic engineering (for example, see Sambrook et al., "Molecular Cloning", Cold Spring Harbor Laboratories (2001)). The gene encoding the tropinone reductase-I of the present invention can be expressed in a microorganism, by introducing the DNA encoding the tropinone reductase-I into a plasmid vector or phage vector that is stable in the microorganism and allowing the genetic information to be transcribed and translated. Preferably, a promoter, a unit for regulating transcription and translation, is placed upstream of the 5' end of the DNA of the present invention, and a terminator is placed downstream of the 3' end of the DNA. The promoter and the terminator should be functional in the microorganism to be utilized as a host. Available vectors, promoters, and terminators for the above-mentioned various microorganisms are described in detail in "Fundamental Course in Microbiology (8): Genetic Engineering," Kyoritsu Shuppan, specifically for yeasts, in Adv. Biochem. Eng. 43, 75-102 (1990) and Yeast 8, 423-488 (1992).

For example, for the genus *Escherichia*, in particular, for *Escherichia coli*, available plasmids include pBR series and pUC series plasmids; available promoters include promoters derived from lac (derived from β-galactosidase gene), trp (derived from the tryptophan operon), tac and trc (which are chimeras of lac and trp), $P_L$ and $P_R$ of λ phage, etc. Available terminators are derived from trpA, phages, rrnB ribosomal RNA, etc. Among these, pSE420D vector (described in JP-A 2000-189170) can be used preferably, that is, obtained from commercially available pSE420 vector (Invitrogen) by partially modifying its multi-cloning site.

For the genus *Bacillus*, available vectors are pUB110 series and pC194 series plasmids; the vectors can be integrated into host chromosome. Available promoters and terminators are derived from apr (alkaline protease), npr (neutral protease), amy (α-amylase), etc.

For the genus *Pseudomonas*, there are host-vector systems developed for *Pseudomonas putida* and *Pseudomonas cepacia*. A broad-host-range vector, pKT240, (containing RSF1010-derived genes required for autonomous replication) based on TOL plasmid, which is involved in decomposition of toluene compounds, is available; a promoter and a terminator derived from the lipase gene (JP-A No. Hei 5-284973) are available.

For the genus *Brevibacterium*, in particular, for *Brevibacterium lactofermentum*, available plasmid vectors include pAJ43 (Gene 39, 281 (1985)). Promoters and terminators used for *Escherichia coli* can be utilized without any modification for *Brevibacterium*.

For the genus *Corynebacterium*, in particular, for *Corynebacterium glutamicum*, plasmid vectors such as pCS11 (JP-A Sho 57-183799) and pCB101 (Mol. Gen. Genet. 196, 175 (1984)) are available.

For the genus *Streptococcus*, plasmid vectors such as pHV1301 (FEMS Microbiol. Lett. 26, 239 (1985)) and pGK1 (Appl. Environ. Microbiol. 50, 94 (1985)) can be used.

For the genus *Lactobacillus*, plasmid vectors such as pAMβ1 (J. Bacteriol. 137, 614 (1979)), which was developed for the genus *Streptococcus*, can be utilized; and promoters that are used for *Escherichia coli* are also usable.

For the genus *Rhodococcus*, plasmid vectors isolated from *Rhodococcus rhodochrous* are available (J. Gen. Microbiol. 138, 1003 (1992)).

For the genus *Streptomyces*, plasmids can be constructed in accordance with the method as described in Hopwood et al., "Genetic Manipulation of *Streptomyces*: A Laboratory Manual" (Cold Spring Harbor Laboratories (1985)). In particular, for *Streptomyces lividans*, pIJ486 (Mol. Gen. Genet. 203, 468-478, 1986), pKC1064 (Gene 103, 97-99 (1991)), and pUWL-KS (Gene 165, 149-150 (1995)) are usable. The same plasmids can also be utilized for *Streptomyces virginiae* (Actinomycetol. 11, 46-53 (1997)).

For the genus *Saccharomyces*, in particular, for *Saccharomyces cerevisiae*, YRp series, YEp series, YCp series, and YIp series plasmids are available; integration vectors (refer EP 537456, etc.), which are integrated into chromosome via homologous recombination with multicopy-ribosomal genes, allow to introduce a gene of interest in multicopy and the gene incorporated is stably maintained in the microorganism; and thus, these types of vectors are highly useful. Available promoters and terminators are derived from genes encoding ADH (alcohol dehydrogenase), GAPDH (glyceraldehyde-3-phosphate dehydrogenase), PHO (acid phosphatase), GAL (β-galactosidase), PGK (phosphoglycerate kinase), ENO (enolase), etc.

For the genus *Kluyveromyces*, in particular, for *Kluyveromyces lactis*, available plasmids are those such as 2-μm plasmids derived from *Saccharomyces cerevisiae*, pKD1 series plasmids (J. Bacteriol. 145, 382-390 (1981)), plasmids derived from pGK11 and involved in the killer activity, KARS (Kluyveromyces autonomous replication sequence) plasmids, and plasmids (refer EP 537456, etc.) capable of being integrated into chromosome via homologous recombination with the ribosomal DNA. Promoters and terminators derived from ADH, PGK, and the like are available.

For the genus *Schizosaccharomyces*, it is possible to use plasmid vectors comprising ARS (autonomous replication sequence) derived from *Schizosaccharomyces pombe* and auxotrophy-complementing selectable markers derived from *Saccharomyces cerevisiae* (Mol. Cell. Biol. 6, 80 (1986)). Promoters such as ADH promoter derived from *Schizosaccharomyces pombe* are usable (EMBO J. 6, 729 (1987)). In particular, pAUR224 is commercially available from TaKaRa Shuzo Co., Ltd.

For the genus *Zygosaccharomyces*, plasmids originating from those such as pSB3 (Nucleic Acids Res. 13, 4267 (1985)) derived from *Zygosaccharomyces rouxii* are available; it is possible to use promoters such as PHO5 promoter derived from *Saccharomyces cerevisiae* and GAP-Zr (Glyceraldehyde-3-phosphate dehydrogenase) promoter (Agri. Biol. Chem. 54, 2521 (1990)) derived from *Zygosaccharomyces rouxii*.

For the genus *Pichia*, host-vector systems originating from autonomous replication sequences (PARS1, PARS2) derived from *Pichia* have been developed (Mol. Cell. Biol. 5, 3376 (1985)), and it is possible to employ a highly efficient promoter such as methanol-inducible AOX promoter, which is available for high-cell-density-culture (Nucleic Acids Res. 15, 3859 (1987)). Host vector system is developed for *Pichia angusta* (previously called *Hansenula polymorpha*). Although autonomous replication sequences (HARS1 and HARS2) derived from *Pichia angusta* are available as vectors, they are rather unstable. Therefore, multicopy integration to chromosome is effective for them (Yeast 7, 431-443 (1991)). In addition, promoters of AOX (alcohol oxidase) and FDH (formate dehydrogenase) induced by methanol and such are available.

For the genus *Candida*, host-vector systems have been developed for *Candida maltosa*, *Candida albicans*, *Candida tropicalis*, *Candida utilis*, etc. An autonomous replication sequence originating from *Candida maltosa* has been cloned (Agri. Biol. Chem. 51, 51, 1587 (1987)), and a vector using the sequence has been developed for *Candida maltosa*. Further, a chromosome-integration vector with a highly efficient promoter unit has been developed for *Candida utilis* (JP-A Hei 08-173170).

For the genus *Aspergillus*, *Aspergillus niger* and *Aspergillus oryzae* have intensively been studied among fungi, and thus plasmid vectors and chromosome-integration vectors are available, as well as promoters derived from an extracellular protease gene and amylase gene (Trends in Biotechnology 7, 283-287 (1989)).

For the genus *Trichoderma*, host-vector systems have been developed for *Trichoderma reesei*, and promoters such as that derived from an extracellular cellulase gene are available (Biotechnology 7, 596-603 (1989)).

There are various host-vector systems developed for plants and animals other than microorganisms; in particular, the systems include those of insect such as silkworm (Nature 315, 592-594 (1985)), and plants such as rapeseed, maize, potato, etc. These systems are preferably employed to express a large amount of foreign protein. According to the known method in the art, the transformants can be cultured and tropinone reductase-I can be purified from the transformants.

The method of the present invention for producing optically active alcohols can be used in combination with a system of coenzyme regeneration. The tropinone reductase-I requires a reduced coenzyme in the process of ketone reduction to produce alcohols. Such reduced coenzymes include NADPH and NADH. For example, when NAD(P)H is used as a reduced coenzyme, NAD(P)$^+$ is generated from NAD(P)H during the reduction by tropinone reductase-I. NAD(P)$^+$ can be converted to the reduced form NAD(P)H using an appropriate substrate-oxidation reaction. The regeneration of NAD(P)H from NAD(P)$^+$ can be achieved by using an NAD(P)H-regenerating enzyme derived from plants, microorganisms, or transformants. NAD(P)H regeneration may be a single-step reaction using a single enzyme catalyzing the regeneration, or a multi-step reaction comprising two or more enzymes. When a reaction of interest comprises two or more enzymes, the enzymes of the series of enzymatic reaction steps are collectively referred to as "enzyme system."

The NAD(P)$^+$-reducing potency can be enhanced by adding, to the reaction system, a sugar such as glucose or sucrose, organic acid, or alcohol such as ethanol or isopropanol. The regeneration of NAD(P)H can also be achieved by using an enzyme capable of converting NAD(P)$^+$ to NAD(P)H. Enzymes useful for NAD(P)H generation are listed below. Microorganisms containing such an enzyme, processed product thereof, or the partially purified enzymes can be used in addition to the purified enzymes. For example, when the enzyme is glucose dehydrogenase, NAD(P)H is regenerated from NAD(P)$^+$ accompanied by the oxidation of glucose to δ-gluconolactone.

Glucose dehydrogenase
Glutamate dehydrogenase
Formate dehydrogenase
Malate dehydrogenase
Glucose-6-phosphate dehydrogenase
Phosphogluconate dehydrogenase
Alcohol dehydrogenase
Glycerol dehydrogenase Directly or after immobilization, each of the enzymes required for NAD(P)H regeneration may be added to the reductase reaction system of the present invention. Alternatively, the enzymes can be contacted with the above-mentioned reaction system through an NAD(P)H-permeable membrane.

When a transformant carrying a recombinant vector containing the DNA encoding tropinone reductase-I is used according to the method of the present invention for producing optically active alcohols, the auxiliary reaction system of NAD(P)H regeneration may be dispensable in some cases. Namely, when an organism containing the high activity of regenerating NAD(P)H is used as the host, the efficient reduction can be achieved using the transformant without adding the enzyme for NAD(P)H regeneration.

Alternatively, it is possible to use a host where the DNA encoding tropinone reductase-I has been co-introduced with the gene encoding the above-mentioned enzyme for NAD(P)H regeneration. The use of such a transformant allows more efficient substrate reduction as well as expression of the NAD(P)H-regenerating enzyme and tropinone reductase-I. Two or more genes can be introduced into a host by a known method such as a method where the host is transformed with multiple recombinant vectors having distinct replication origins into which the respective genes have been inserted separately to avoid the incompatibility; a method where both genes have been inserted into a single vector; a method where one or both genes are integrated into a chromosome of the host.

Glucose dehydrogenases that can be used for NAD(P)H regeneration in the present invention include glucose dehydrogenases derived from *Bacillus subtilis* and *Thermoplasma acidophilum*. The genes encoding the enzymes are already isolated (Proc. Natl. Acad. Sci. U.S.A., 80, 785-789 (1983); Eur. J. Biochem., 211, 549-554 (1993)). The genes can also be obtained from the microorganisms by PCR or hybridization screening based on the known nucleotide sequences.

When multiple genes are inserted into a single vector, regions responsible for expressional regulation such as promoter and terminator may be ligated to each gene, or alternatively the genes can be expressed as an operon containing multiple cistrons like the lactose operon.

A single vector in which the genes encoding tropinone reductase-I and glucose dehydrogenase have been inserted can be prepared, for example, by ligating both genes in tandem into pSE420D (JP-A 2000-189170). The plasmid pSG-DSR1 (FERM BP-8061) which contains *Datura stramonium*-derived tropinone reductase-I and *Bacillus subtilis*-derived glucose dehydrogenase genes as inserts, and the plasmid pSG-HNR1 (FERM BP-8062) which contains *Hyoscyamus niger*-derived tropinone reductase-I and *Bacillus subtilis*-derived glucose dehydrogenase genes as inserts, have been deposited under the following conditions under the Budapest Treaty.

Deposition of Plasmids pSG-DSR1 and pSG-HNR1:
(a) Name and Address of Depositary Institute Name: International Patent Organism Depositary, National Institute of Advanced Industrial Science and Technology (AIST), Independent Administrative Institution (Previous Name: The National Institute of Bioscience and Human-Technology, The Agency of Industrial Science and Technology, The Ministry of International Trade and Industry (1-1-3 Higashi, Tsukuba, Ibaraki, Japan))

Address: Chuo 6, 1-1-3 Higashi, Tsukuba, Ibaraki, Japan (Post code: 305-8566)

(b) Depositary date: May, 28, 2002 (original deposit was made on Jun. 22, 2001)

(c) Accession number: FERM BP-8061 (pSG-DSR1)
Accession number: FERM BP-8062 (pSG-HNR1)

It is often difficult to co-express enzyme genes of different origins. As seen from the example of co-expression of *Pichia finlandica*-derived (R)-2-octanol dehydrogenase and *Bacillus subtilis*-derived glucose dehydrogenase whose genes have been inserted in pSG-PFO1 or pSG-PFO2 (WO 01/61014), the expression levels of the two enzymes are not always high. Furthermore, it is generally accepted that a plant-derived enzyme or an enzyme derived from an organism other than plants is hardly co-expressed. Thus, it has not been obvious to obtain a transformant co-expressing tropinone reductase-I and glucose dehydrogenase, which is useful for practicing the above-mentioned production method of the present invention.

However, the present inventors succeeded in obtaining a transformant carrying a vector encompassing tropinone reductase-I and glucose dehydrogenase genes ligated in tandem, which enables asymmetric reduction of 3-quinuclidinone at a concentration of as high as 10%. Herein, unless otherwise specified, "%" for concentration means "w/v %."

The present invention provides a vector containing and capable of expressing a DNA encoding tropinone reductase-I and a DNA encoding an enzyme that regenerates an oxidized coenzyme to its reduced form.

The DNA encoding tropinone reductase-I to be inserted into the vector of the present invention can be, for example, a DNA selected from the group consisting of (a) to (d):

(a) a DNA comprising the nucleotide sequence of SEQ ID NO: 1 or SEQ ID NO: 3;

(b) a DNA that encodes a protein comprising the amino acid sequence of SEQ ID NO: 2 or SEQ ID NO: 4 in which one or more amino acids have been substituted, deleted, inserted, and/or added, and having the activity of producing (R)-3-quinuclidinol via asymmetric reduction of 3-quinuclidinone;

(c) a DNA comprising a nucleotide sequence having 85% or higher identity to the nucleotide sequence of SEQ ID NO: 1 or SEQ ID NO: 3, and encoding a protein having the activity of producing (R)-3-quinuclidinol via asymmetric reduction of 3-quinuclidinone; and (d) a DNA that is capable of hybridizing to a polynucleotide comprising the nucleotide sequence of SEQ ID NO: 1 or SEQ ID NO: 3 under a stringent condition, and encodes a protein having the activity of producing (R)-3-quinuclidinol via asymmetric reduction of 3-quinuclidinone.

The above-mentioned regeneration enzyme can be used as the enzyme of regenerating a reduced coenzyme from its oxidized form, which is to be inserted into the vector of the present invention. Particularly, glucose dehydrogenase is a preferred regeneration enzyme. Such dehydrogenases include glucose dehydrogenases derived from *Bacillus subtilis* and *Thermoplasma acidophilum*. As shown in the example herein, when these glucose dehydrogenases are used in combination with a DNA comprising the nucleotide sequence of SEQ ID NO: 1 or SEQ ID NO: 3 which encodes tropinone reductase-I, a transformant containing them can produce a high concentration of (R)-3-quinuclidinol.

It is preferred to ligate DNAs encoding tropinone reductase-I and the regeneration enzyme in tandem in the vector of the present invention. The term "ligate in tandem," as employed herein means arranging the DNAs so as to ensure the expression of these enzymes under the control of a common expressional regulatory region. Such an arrangement allows more efficient expression of the enzyme genes and production of optically active alcohols.

The present invention also relates to a transformant containing and capable of expressing the vector of the present invention. The vector of the present invention may be transformed into arbitrary hosts, so long as the vector is maintained and expressed in the hosts. In the present invention, the most preferred host is a microorganism substantially lacking the ability of producing the optical isomer of the optically active alcohol of interest. For example, when the target optically active alcohol is (R)-3-quinuclidinol, the host can be a microorganism which itself does not substantially produce 3-quinuclidinol. When the host has the activity of synthesizing (S)-3-quinuclidinol, it is preferable to use a mutant strain which is deficient in the enzyme producing the (S) form. The deficient strain can be obtained by the use of spontaneous mutation, artificial mutation, genetic recombination technique, or the like. For example, *E. coli* HB101 strain used herein in Example is a microorganism which originally does not substantially produce the optical isomer of 3-quinuclidinol. Thus, the strain is preferably used as a host microorganism to prepare a transformant which is to be used in the method of the present invention for producing (R)-3-quinuclidinol.

The enzymatic reaction to produce an optically active alcohol according to the method of the present invention can be carried out by contacting the above-mentioned enzymatic material with a reaction solution containing a ketone as the substrate. Specifically, the reaction can be carried out in an aqueous solvent, in a mixed system of an aqueous solvent and a water-soluble organic solvent, or in a two-phase mixed system of an aqueous solvent and a water-insoluble organic solvent. Such aqueous solvents include buffers having buffer capacity at a neutral pH, such as phosphate buffer and Tris-HCl buffer. Alternatively, no buffer is required when the use of acid and alkali can keep the pH change during the reaction within a desired range. Organic solvents insoluble or sparingly insoluble in water that can be used include, for example, ethyl acetate, butyl acetate, toluene, chloroform, n-hexane, isooctane, etc. Alternatively, the reaction can be carried out in a mixed system consisting of an aqueous solvent and an organic solvent such as ethanol, acetone, dimethyl sulfoxide, and acetonitrile.

In such a two-phase system, the enzymatic material is supplied as it is, or as a solution after combined with water or buffer. After dissolved in an aqueous solvent such as water, buffer, or ethanol, a compound used as the substrate can be supplied to the reaction system. In this case, the substrate and enzymatic material react in a single-phase reaction system. Alternatively, the reaction of the present invention may be carried out by using an immobilized enzyme, a membrane reactor, or the like. Membranes that can constitute a membrane reactor are exemplified by ultra-filter, hydrophobic membrane, cationic membrane, nanofiltration membrane (J. Ferment. Bioeng. 83, 54-58 (1997)) etc. The forms of contacting the enzyme with the reaction solution are not limited to these examples. The reaction solution is defined as a solution which is obtained by dissolving a substrate in an appropriate solvent providing a condition preferable for the enzymatic activity.

There is no limitation on the type of ketone, which is the substrate compound of the present invention, so long as it can be converted to an optically active alcohol of interest by the action of tropinone reductase-I. Table 1 lists compounds which are available substrates and alcohols converted from the substrates according to the present invention.

TABLE 1

| Substrate | Alcohol |
| --- | --- |
| Tropinone | Tropine |
| 3-Quinuclidinone | 3-Quinuclidinol |
| 6-Hydroxytropinone | 6-Hydroxytropine |
| N-Methyl-4-piperidone | N-Methyl-4-piperidinol |
| 4-Piperidone | 4-Piperidinol |
| Tetrahydrothiopyran-4-one | Tetrahydrothiopyran-4-ol |
| 4-Methylcyclohexanone | 4-Methylcyclohexanol |
| 3-Methylcyclohexanone | 3-Methylcyclohexanol |
| 2-Methylcyclohexanone | 2-Methylcyclohexanol |
| 4-Ethylcyclohexanone | 4-Ethylcyclohexanol |
| 8-Thiabicyclo[3.2.1]-octan-3-one | 8-Thiabicyclo[3.2.1]-octan-3-ol |
| 7-Hydroxytropinone | 7-Hydroxytropine |
| N-Ethylnortropinone | N-Ethylnortropine |
| N-iso-Propylnortropinone | N-iso-Propylnortropine |

Among these substrates, a particularly preferred example is 3-quinuclidinone. (R)-3-quinuclidinol that is generated from substrate 3-quinuclidinone is an optically active compound that is industrially useful, as described herein earlier.

The structures of 3-quinuclidinone and (R)-3-quinuclidinol are shown in formula (1).

Formula (1):

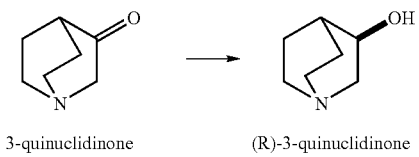

3-quinuclidinone  (R)-3-quinuclidinone

The enzymatic reaction of tropinone reductase-I of the present invention can be carried out under the following conditions.

substrate concentration: 0.01 to 50%, preferably, 0.1 to 30%.

enzyme concentration: 0.01 to 500 U/ml, preferably 1 to 100 U/ml.

reaction temperature: 4 to 60° C., preferably 30 to 50° C.

pH: 4 to 9, preferably 6.5 to 8.5.

When required, the coenzyme NAD(P)$^+$ or NAD(P)H may be added at a concentration of 0.001 to 100 mM, preferably 0.01 to 10 mM, to the reaction system. The substrate may be added to the reaction at once at the start of reaction, or continuously or stepwise.

The substrate for the coenzyme-regenerating enzyme can be added, for example, at a 0.1 to 20 times higher, preferably 0.5 to 5 times higher molar concentration than the substrate ketone. The NAD (P)H-regenerating enzyme can be added at a concentration that ensures approximately 0.1 to 100 times higher, preferably 0.5 to 20 times higher enzymatic activity as compared with tropinone reductase-I. Exemplary combinations of the substrate for regenerating NAD(P)H and the enzyme for NAD(P)H regeneration are shown below.

| Substrate | Enzyme |
| --- | --- |
| Glucose | Glucose dehydrogenase |
| Formic acid | Formate dehydrogenase |
| Ethanol or 2-propanol | Alcohol dehydrogenase |
| L-Glutamic acid | Glutamate dehydrogenase |
| L-Malic acid | Malate dehydrogenase or organic acid dehydrogenase |

Optically active alcohols produced according to the present invention can be collected by well known methods. Such methods include, but are not limited to, separation and purification means such as extraction from a reaction solution with an organic solvent; crystallization; recrystallization; column chromatography; concentration; distillation; etc. The separation and purification means can be used singly or in combination. If required, the collection method can comprise a step of separating cells of microorganism or proteins from the reaction solution. Such separation of cells of microorganism or proteins can be achieved by centrifugal separation, membrane treatment, etc.

Optically active alcohols with high optical purity can be produced on a large scale by the method of the present invention. The crystals of high optical purity products can be obtained readily. For example, (R)-3-quinuclidinol, which is an optically active alcohol, can readily be crystallized as the form of a hydrochloride salt by the method as described below. The present invention also provides a method for obtaining (R)-3-quinuclidinol hydrochloride, the method comprising the steps of:

(a) making the pH of a (R)-3-quinuclidinol solution alkaline to form free (R)-3-quinuclidinol;

(b) extracting free (R)-3-quinuclidinol with n-butanol;

(c) adding hydrochloric acid to the extract;

(d) removing moisture from the extract; and (e) crystallizing (R)-3-quinuclidinol hydrochloride in the solution obtained in (d).

(R)-3-quinuclidinol in the n-butanol extract can be converted into a hydrochloride salt in the above crystallization step by removing moisture from the n-butanol extract, flushing hydrochloric acid gas, then performing crystallization of (R)-3-quinuclidinol hydrochloride from the extract.

Crystals of free (R)-3-quinuclidinol can also be obtained from (R)-3-quinuclidinol hydrochloride obtained by the above method. The present invention provides a method for obtaining crystals of free (R)-3-quinuclidinol, the method comprising the steps of:

(a) dissolving (R)-3-quinuclidinol hydrochloride in a first solvent;

(b) making the pH of the solution described in (a) alkaline to form free (R)-3-quinuclidinol;

(c) adding a second solvent, (d) distilling off the first solvent, (e) crystallizing (R)-3-quinuclidinol in the solution obtained in (d)

wherein the first solvent dissolves (R)-3-quinuclidinol hydrochloride at 1% or higher concentration. The solubility of 1% or higher of (R)-3-quinuclidinol hydrochloride in a solvent is defined as the solubility at a particular temperature at which (R)-3-quinuclidinol hydrochloride is dissolved in the solvent. The second solvent can be substituted for the solvent by distilling off the first solvent, for example, by azeotropic distillation, from a mixture of these solvents, dissolves free (R)-3-quinuclidinol with lower solubility than the first solvent, and allows crystallizing free (R)-3-quinuclidinol from itself. The term "solvent" that allows to crystallize 3-quinuclidinol" means a solvent that ensures the production of 3-quinuclidinol crystals when the solubility of 3-quinuclidinol is decreased by decreasing the solvent temperature, or the solvent is removed.

In the above-mentioned crystallization step, for example, any solvent selected from the group consisting of toluene, hexane, 4-methyl-2-pentanone, and butyl acetate may be used as the second solvent, singly or in combination of two or more of these. The combination where the first solvent is water and the second solvent is toluene is particularly preferred.

The method of the present invention for yielding (R)-3-quinuclidinol hydrochloride is described in more detail. The (R)-3-quinuclidinol solution used as a starting material can be provided by dissolving (R)-3-quinuclidinol in an aqueous solvent such as water, a buffer having buffer capacity at a neutral pH, such as phosphate buffer and Tris-HCl buffer. Alternatively, the reaction solution of the above enzymatic reaction can be used as the starting (R)-3-quinuclidinol solution. The concentration of (R)-3-quinuclidinol in the starting solution ranges from 1 to 80%. When required, cells of microorganism or proteins can be separated from the reaction solution containing (R)-3-quinuclidinol by centrifugal separation, membrane treatment, or the like. Then, pH of the reaction solution is made alkaline by adding alkali. Such alkalis that can be used includes sodium hydroxide and potassium hydroxide. The pH is adjusted to 10 or higher, preferably 12 or higher. (R)-3-quinuclidinol is converted to the free form by this step of alkalifying the reaction solution.

Free (R)-3-quinuclidinol is extracted from the reaction solution with n-butanol. When 0.8 to 5 molar equivalent, preferably 1 to 1.2 molar equivalent excess of hydrochloric acid is added to one molar equivalent of (R)-3-quinuclidinol in the n-butanol extract, (R)-3-quinuclidinol is converted to a hydrochloride salt. Then, moisture is removed from the solution by azeotropic dehydration. (R)-3-quinuclidinol hydrochloride can be crystallized in the resulting solution by cooling the solution.

It is possible to crystallize free (R)-3-quinuclidinol from the hydrochloride salt obtained by the procedure as described above. For example, the hydrochloride salt is dissolved in 0.5 volumes or higher, preferably 0.8 to 1.5 volumes of the first solvent. The first solvent is preferably water. The resulting (R)-3-quinuclidinol solution is combined with an alkali. The alkali may be sodium hydroxide or potassium hydroxide. The pH of the (R)-3-quinuclidinol solution is adjusted to 10 or higher, preferably 12 or higher. Alkalization of the reaction solution converts (R)-3-quinuclidinol hydrochloride to its free form. Free (R)-3-quinuclidinol can be crystallized from the second solvent that is an appropriate organic solvent.

For example, one or more volumes of, preferably 5 to 50 volumes of toluene is added as the second solvent to the (R)-3-quinuclidinol solution, and then the first solvent is distilled off. If required, impurities generated during the treatment, such as inorganic salts, are separated by a method such as filtration. By cooling, for example, (R)-3-quinuclidinol can be crystallized from the remaining toluene. Separation of impurities is preferably carried out by filtration under heating to prevent yield reduction. Hexane, 4-methyl-2-pentanone, butyl acetate, or the like, in addition to toluene, can be used as the second solvent.

(R)-3-quinuclidinol that can be obtained according to the present invention can be crystallized as the free form as well as the form of a hydrochloride salt. Namely, the present invention provides a method for producing (R)-3-quinuclidinol, the method comprising the steps of:

(a) making the pH of (R)-3-quinuclidinol solution alkaline to form free (R)-3-quinuclidinol;
(b) extracting free (R)-3-quinuclidinol with n-butanol; and
(c) adding an organic solvent to the extract;
(d) distilling off n-butanol from the extract; and
(e) crystallizing (R)-3-quinuclidinol from the solution obtained in (d).

The method of the present invention for yielding crystals of free (R)-3-quinuclidinol is described in more detail. The steps (a) and (b) can be performed in the same manner as in the above-described method for yielding (R)-3-quinuclidinol hydrochloride. For example, (R)-3-quinuclidinol produced by the method according to the present invention as described herein earlier is converted to its free form by adding an alkali. Free (R)-3-quinuclidinol is extracted with n-butanol, and then moisture is removed from the solution by azeotropic dehydration. Further, 3 to 100 volumes of, preferably 5 to 10 volumes of an organic solvent is added to the n-butanol extract. As the organic solvent, those exemplified for the second solvent as described above can be used and include toluene, hexane, 4-methyl-2-pentanone, butyl acetate, etc. Toluene is particularly preferred.

After water and n-butanol are removed by the azeotropic treatment, when required, impurities are removed by filtration or the like. Then, (R)-3-quinuclidinol can be crystallized in the resulting solution by cooling. The removal of impurities is preferably carried out by filtration under heating to prevent yield reduction.

For industrial purposes, it is essential to produce high-purity crystals. High-purity (R)-3-quinuclidinol can be obtained by removing impurities via crystallization.

The present invention provides a method for producing optically active alcohols using the asymmetric reduction activity of tropinone reductase-I. This method enables simple and efficient production of (R)-3-quinuclidinol that is an industrially important compound. In addition, (R)-3-quinuclidinol obtained according to the present invention has high optical purity.

Further, the present invention provides a more efficient method for producing (R)-3-quinuclidinol by using genetic recombination techniques. The method of the present invention for producing optically active alcohols can be implemented further efficiently when tropinone reductase-I is co-expressed with an enzyme regenerating an oxidized coenzyme. Optically active alcohols can be produced highly efficiently by co-expressing, for example, tropinone reductase-I derived from a plant such as *Datura stramonium* or *Hyoscyamus niger* and glucose dehydrogenase, as a regeneration enzyme, derived from *Bacillus subtilis* or *Thermoplasma acidophilum*. It had been difficult to predict whether co-expression of the plant-derived enzyme and the microorganism-derived enzyme allowed highly efficient production of (R)-3-quinuclidinol with high optical purity.

Furthermore, the present invention provides a method to crystallize (R)-3-quinuclidinol with high optical purity. Since high optical purity (R)-3-quinuclidinol is obtained at a high concentration according to the present invention, the compound can be efficiently crystallized. In addition, the present inventors found that particular combinations of solvents allowed to readily crystallize (R)-3-quinuclidinol, which is generally difficult to be crystallized due to high solubility in aqueous solutions. Preparing substances as high purity crystals is essential for their industrial use.

All publications describing prior art cited herein are incorporated herein by reference.

The present invention is illustrated in detail below with reference to Examples, but is not to be construed as being limited thereto.

Example 1

Isolation of *Datura stramonium* Tropinone Reductase-I Gene pETTR1 containing the gene encoding tropinone reductase-I from *Datura stramonium* was isolated according to the method as described in a literature (Proc. Natl. Acad. Sci. U.S.A., 95, 4876-4881 (1998)). In order to newly construct a plasmid, the primers DSR-ATG1 (SEQ ID NO: 5) and DSR-TAA1 (SEQ ID NO: 6) were synthesized based on the 5'-end and 3'-end sequences of the structural gene. Using pETTR1 as a template, a specific DNA was amplified by PCR (30 cycles of denaturation at 95° C. for 30 seconds, annealing at 50° C. for 1 minute, and extension at 75° C. for 3 minutes and 15 seconds).

```
SEQ ID NO: 5: DSR-ATG1/
ATACCATGGAAGAATCAAAAGTG

SEQ ID NO: 6: DSR-TAA1/
TGGTCTAGATTAAAACCCACCATTAGCTGTG
```

Example 2

Construction of Plasmid pSG-DSR1 for Co-Expression of *Datura stramonium*-Derived Tropinone Reductase-I and *Bacillus subtilis*-Derived Glucose Dehydrogenase Genes The plasmid pSE-BSG1 (JP-A 2000-189170) containing the glucose dehydrogenase gene derived from *Bacillus subtilis* was double-digested with the restriction enzymes NcoI and XbaI, and thus a DNA fragment containing the glucose dehydrogenase gene derived from *Bacillus subtilis* was prepared. The DNA fragment was ligated, by using T4 DNA ligase, to a DNA fragment containing the tropinone reductase-I gene derived from *Datura stramonium* that had been obtained by digesting the DNA fragment prepared in Example 1 with the same enzymes. The plasmid pSG-DSR1 (FERM BP-8061), which allows co-expression of glucose dehydrogenase and tropinone reductase-I, was thus obtained.

Example 3

Co-Expression of *Datura stramonium*-Derived Tropinone Reductase-I and *Bacillus subtilis*-Derived Glucose Dehydrogenase

*E. coli* HB101 strain transformed with pSG-DSR1 (*E. coli* HB101 (pSG-DSR1)) was cultured overnight in LB medium containing 50 mg/L ampicillin. 0.1 mM IPTG was added to the culture to induce the expression of genes. Then, the bacterial cells were further cultured for 4 hours. After harvesting, the bacterial cells were crushed in a closed chamber-type sonicator UCD-200™ (Cosmo Bio). The supernatant obtained by centrifugation was used as a cell-free extract.

Example 4

Enzymatic Activities of *Datura stramonium*-Derived Tropinone Reductase-I and *Bacillus subtilis*-Derived Glucose Dehydrogenase Enzymatic activities of the cell-free extract obtained in Example 3 were assayed. The cell-free extract derived from the recombinant *E. coli* cells showed tropinone-reducing activity in an NADPH-dependent fashion, and the specific activity was 9.49 U/mg protein. Further, the cell-free extract derived from the recombinant *E. coli* cells showed 3-quinuclidinone-reducing activity in an NADPH-dependent fashion, and the specific activity was 4.33 U/mg protein.

The assay for glucose dehydrogenase activity was carried out by incubating a reaction solution containing 100 mM potassium phosphate buffer (pH 6.5), 2.5 mM $NAD^+$, 100 mM D-glucose, and the cell-free extract at 37° C. 1 U was defined as an enzyme amount capable of catalyzing the generation of 1 μmol NADH for 1 minute. The cell-free extract derived from the recombinant *E. coli* cells showed the specific activity of 9.02 U/mg protein.

Example 5

Synthesis of (R)-3-Quinuclidinol Using *Datura stramonium*-Derived Tropinone Reductase-I Cells of *E. coli* transformed with pSG-DSR1 prepared in Example 2 were cultured in 400 mL of 2×YT medium (Tryptone 20 g, Yeast extract 10 g, NaCl 10 g, pH 7.2). After the expression was induced with 0.1 mM IPTG, the cells were harvested. The bacterial cells obtained were added to 400 mL of a reaction solution containing 500 mM potassium phosphate buffer (pH 7.5), 10% (618.7 mM) 3-quinuclidinone hydrochloride, and 927.8 mM glucose, and the mixture was incubated at 37° C. overnight while being agitated.

After the bacterial cells were removed, an aliquot of the reaction solution was diluted twice with 0.35 N sodium hydroxide, 3-quinuclidinol produced was quantified by gas chromatography. The gas chromatography analysis was carried out by using Unisol 10T+KOH (10+3%) Uniport HP 80/100 Mesh (2 m, GL Sciences, Inc.). Column temperature was 150° C., and detection temperature was 250° C. The detector used was a Flame Ionization Detector (FID). The retention time for each compound was as follows: 3-quinuclidinone, 5.4 minutes; 3-quinuclidinol, 11.2 minutes. Further, the concentration of 3-quinuclidinol hydrochloride computed based on the signal intensity was 89.5 g/L, and the yield was 88.4%.

Then, the optical purity of products was determined. An assay for the optical purity was carried out by the following procedure. First, after the bacterial cells were removed from the reaction solution, sodium carbonate was added to the solution to a saturated concentration and 3-quinuclidinol was extracted with ethyl acetate. After desolvation, the product was benzoylated with benzoyl chloride, and then analyzed by high-performance liquid chromatography using an optical resolution column (column: CHIRALPACK AD from Daicel Chemical Industries LTD.; mobile phase, n-hexane/ethanol/diethyl amine (95/5/0.1); detection wavelength, 254 nm; flow rate, 1.0 mL/minute). The (S) form was detected with the retention time of 12 minutes; the (R) form was detected with 23 minutes. The result showed that the optical purity of the product was 98.6% ee (R).

Further, after the bacterial cells were removed from the reaction solution, sodium carbonate was added to the solution to a saturated concentration and 3-quinuclidinol was extracted twice with ethyl acetate. The crystals obtained after desolvation were dissolved in 1N hydrochloric acid, and then its optical rotation was determined.

The result showed: $[\alpha]_D=-43.7$ (c=1, 1N HCl). The product was verified to be the (R) form by comparing the value with that previously reported in a literature ($[\alpha]_D=-43.8$ (c=3, 1N HCl); J. Amer. Chem. Soc., 74, 2215-2218 (1952)).

Example 6

Recovery of (R)-3-Quinuclidinol Hydrochloride from the Reaction Solution

The bacterial cells were removed by centrifugal separation from the reaction solution prepared in Example 5, the solution was deproteinized by the treatment with an UF membrane and concentrated with an evaporator. The pH of the solution was adjusted to 12.0 by adding 25% sodium hydroxide thereto, and then the solution was extracted twice with an equal volume of n-butanol. A 18 mL portion of concentrated hydrochloric acid was added to the extract, and water was removed by distillation at 110 to 130° C. under normal pressure. Crystals of (R)-3-quinuclidinol hydrochloride were obtained by cooling. The resulting crystals were collected by filtration, and dried under reduced pressure. The quantity of crystals obtained was 32.4 g, and the yield was 80.0%.

Example 7

Conversion of (R)-3-Quinuclidinol Hydrochloride to its Free Form

The crystals of (R)-3-quinuclidinol hydrochloride prepared in Example 6 (25.0 g) was dissolved in 25.0 g water, then the pH of the solution was adjusted to 13.0 by adding 25% sodium hydroxide. Toluene (500 g) was added to the solution, and the mixture was treated by azeotropic dehydration at 60 to 70° C. under 170 Torr. After dehydration, (R)-3-quinuclidinol was completely dissolved in toluene at 80° C. under normal pressure, and the residual inorganic salts were removed by filtration with heating at 80° C. (R)-3-quinuclidinol crystals were obtained by cooling the toluene solution. The resulting crystals were collected by filtration, and dried under reduced pressure. The quantity of crystals thus obtained was 16 g.

Example 8

Isolation of (R)-3-Quinuclidinol from a Reaction Solution

The bacterial cells were removed by centrifugal separation from a reaction solution of 3-quinuclidinone reduction by *E. coli*, which had been transformed with pSG-DSR1. The solution was deproteinized by the treatment with an UF membrane. The resulting solution (91 g, the content of 3-quinuclidinol hydrochloride was 12%) was combined with a 25% aqueous solution of sodium hydroxide, and then the mixture was adjusted to pH 12. The resulting solution was concentrated to 48 g at 50 to 60° C. under reduced pressure of 20 Torr. An equal volume of n-butanol was added to the solution and the extraction was performed twice. The resulting organic layer was concentrated at 50 to 60° C. under 20 Torr. The cycle of addition of 50 g toluene and concentration was repeated, thereby replacing the solvent with toluene. Following this, the toluene solution was then cooled down and precipitated crystals collected via filtration. The wet crystals were then dried under reduced pressure. The quantity of (R)-3-quinuclidinol yielded as crystals was 6.5 g.

Example 9

Isolation of Tropinone Reductase-I Gene Derived from *Hyoscyamus niger*

The tropinone reductase-I gene derived from *Hyoscyamus niger* was isolated according to the method as described in a literature (Biosci. Biotechnol. Biochem., 63(10), 1819-1822 (1999)). The primers HNR-ATG1 (SEQ ID NO: 7) and HNR-TAA1 (SEQ ID NO: 8) were synthesized based on the 5'-end and 3'-end sequences of the structural gene. A specific DNA was amplified by PCR (30 cycles of denaturation at 95° C. for 30 seconds, annealing at 50° C. for 1 minute, and extension at 75° C. for 3 minutes and 15 seconds) using a tropinone reductase-I cDNA as a template.

```
SEQ ID NO: 7: HNR-ATG1
ATACCATGGCCGGAGAATCA

SEQ ID NO: 8: HNR-TAA1
ACCTCTAGATTAAAACCCACCATTAGCTGTG
```

Example 10

Construction of Plasmid pSG-HNR1 for Co-Expression of *Hyoscyamus niger*-Derived Tropinone Reductase-I and *Bacillus subtilis*-Derived Glucose Dehydrogenase Genes The plasmid pSE-BSG1 (JP-A 2000-189170) containing the glucose dehydrogenase gene derived from *Bacillus subtilis* was double-digested with the restriction enzymes NcoI and XbaI, and thus a DNA fragment containing the glucose dehydrogenase gene derived from *Bacillus subtilis* was prepared. The DNA fragment was ligated, by using T4 DNA ligase, to a DNA fragment containing the tropinone reductase-I gene derived from *Hyoscyamus niger* that had been obtained by digesting the DNA fragment prepared in Example 6 with the same enzymes. The plasmid pSG-HNR1 (FERM BP-8062), which allows co-expression of glucose dehydrogenase and tropinone reductase-I, was thus obtained.

Example 11

Co-Expression of *Hyoscyamus niger*-Derived Tropinone Reductase-I and *Bacillus subtilis*-Derived Glucose Dehydrogenase

*E. coli* HB101 strain transformed with pSG-HNR1 (*E. coli* HB101 (pSG-HNR1)) was cultured overnight in LB medium containing 50 mg/L ampicillin. 0.1 mM IPTG was added to the culture to induce the expression of genes. Thereafter, the bacterial cells were further cultured for 4 hours. After harvesting, the bacterial cells were crushed in a closed chamber-type sonicator UCD-200™ (Cosmo Bio). The supernatant obtained by centrifugation was used as a cell-free extract.

Example 12

Enzymatic Activities of *Hyoscyamus niger*-Derived Tropinone Reductase-I and *Bacillus subtilis*-Derived Glucose Dehydrogenase The enzymatic activity of the cell-free extract obtained in Example 11 was assayed. The cell-free extract derived from the recombinant *E. coli* cells showed tropinone-reducing activity in an NADPH-dependent fashion, and the specific activity was 0.35 U/mg protein.

Furthermore, the cell-free extract derived from the recombinant *E. coli* showed 3-quinuclidinone-reducing activity in an NADPH-dependent fashion, and the specific activity was 0.26 U/mg protein. The specific activity of glucose dehydrogenase was 3.96 U/mg protein. The assay for glucose dehydrogenase activity was carried out by the method as described in Example 4.

Example 13

Synthesis of (R)-3-Quinuclidinol Using *Hyoscyamus niger*-Derived Tropinone Reductase-I

*E. coli* transformed with pSG-HNR1 prepared in Example 9 was cultured in 10 mL of 2×YT medium (Tryptone 20 g, Yeast extract 10 g, NaCl 10 g, pH 7.2). After the expression was induced with 0.1 mM IPTG, the cells were harvested. The bacterial cells obtained were added to 10 mL of a reaction solution containing 500 mM potassium phosphate (pH 6.5), 1% (61.9 mM) 3-quinuclidinone hydrochloride, and 278.4 mM glucose, and the mixture was incubated at 20° C. overnight while being agitated.

After the bacterial cells were removed, 3-quinuclidinol produced was quantified by the method as described in Example 5. The result showed that the concentration of 3-quinuclidinol hydrochloride was 1.59 g/L and the yield was 15.7%.

The optical purity was determined by the method as descried in Example 5. The result showed that the optical purity was 89.0% ee (R).

Example 14

Preparation of Chromosomal DNA from *Thermoplasma acidophilum* IFO 15155

*Thermoplasma acidophilum* IFO 15155 was inoculated into four 250-mL flasks each containing 50 mL of Medium 280 (3 g/L KH$_2$PO$_4$, 0.5 g/L MgSO$_4$.7H$_2$O, 0.25 g/L CaCl$_2$-2H$_2$O, 1 g/L yeast extract, 10 g/L glucose, and 2 g/L (NH$_4$)$_2$SO$_4$ (pH 2.0)). The cells were incubated at 60° C. for two weeks.

The cells were harvested by centrifugal separation, and the chromosomal DNA was prepared with a DNeasy Tissue kit (Qiagen).

Example 15

Cloning of the Glucose Dehydrogenase Gene from *Thermoplasma acidophilum* IFO 15155

In order to clone the glucose dehydrogenase gene from *Thermoplasma acidophilum* IFO 15155, the primers TAG-ATG1 (SEQ ID NO: 9) and TAG-TAA3 (SEQ ID NO: 10) were synthesized.

```
SEQ ID NO: 9: TAG-ATG1
CAGGAATTCAATAATGACTGAACAGAAAGCCATTG

SEQ ID NO: 10: TAG-TAA3
CTGACTAGTATTACTGCCACTTTATCACCGTC
```

A DNA fragment containing the glucose dehydrogenase gene was amplified by PCR (30 cycles of denaturation at 95° C. for 30 seconds, annealing at 50° C. for 1 minute, and extension at 75° C. for 4 minutes) in a reaction solution containing a buffer for Pfu DNA Polymerase, 0.2 mM dNTP, primer DNAs (25 μmol each), 2.5 U Pfu DNA polymerase, and 50 ng of the chromosomal DNA prepared from *Thermoplasma acidophilum* in Example 13.

The DNA fragment obtained was purified with a GFX-column (Pharmacia), and double-digested with EcoRI and SpeI. Then, the DNA fragment was purified by agarose gel electrophoresis.

The DNA fragment obtained was ligated to pSE420D (JP-A 2000-189170) that had been digested with the same restriction enzymes, and thus pSE-TAG3 was constructed.

Example 16

Construction of plasmid pTG-DSR1 for Co-Expression of *Datura*-Derived Tropinone Reductase-I and *Thermoplasma acidophilum* IFO 15155-Derived Glucose Dehydrogenase Genes The plasmid pSG-DSR1 prepared in Example 2 was double-digested with NcoI and XbaI, and then an 824-bp DNA fragment (pSG-DSR1/NcoI-XbaI), which contained the tropinone reductase-I gene derived from *Datura*, was purified. The DNA fragment was ligated, by using T4 DNA ligase, to the vector that was prepared by double-digesting the plasmid pSE-TAG3 obtained in Example 14 with NcoI and XbaI. The plasmid pTG-DSR1, which allows co-expression of glucose dehydrogenase and tropinone reductase-I, was thus obtained.

Example 17

Co-Expression of Tropinone Reductase-I Derived from *Datura* and Glucose Dehydrogenase Derived from *Thermoplasma acidophilum* IFO 15155

*E. coli* HB101 strain transformed with pTG-DSR1 (*E. coli* HB101 (pTG-DSR1)) was cultured overnight in LB medium containing 50 mg/L ampicillin. After 0.1 mM IPTG was added, the bacterial cells were further cultured for 4 hours.

After harvesting, the bacterial cells were crushed in a closed chamber-type sonicator UCD-200™ (Cosmo Bio). The supernatant obtained by centrifugation was used as a cell-free extract.

Example 18

Enzymatic Activities of *Datura*-Derived Tropinone Reductase-I and *Thermoplasma acidophilum* IFO 15155-Derived Glucose Dehydrogenase Enzymatic activities of the cell-free extract obtained in Example 17 were assayed. The cell-free extract derived from the recombinant *E. coli* cells showed tropinone-reducing activity in an NADPH-dependent fashion, and the specific activity was 5.13 U/mg protein.

Further, the cell-free extract derived from the recombinant *E. coli* showed 3-quinuclidinone-reducing activity in an NADPH-dependent fashion, and the specific activity was 1.91 U/mg protein.

The assay for glucose dehydrogenase activity was carried out by incubating a reaction solution containing 100 mM potassium phosphate buffer (pH 7.0), 2.5 mM NADP$^+$, 100 mM D-glucose, and the cell-free extract at 25° C. 1 U was defined as an enzyme amount capable of catalyzing the generation of 1 μmol NADPH for 1 minute.

The specific activity of the cell-free extract derived from the recombinant *E. coli* was 1.95 U/mg protein.

Example 19

Synthesis of (R)-3-Quinuclidinol Using Tropinone Reductase-I Derived from *Datura* and Glucose Dehydrogenase Derived from *Thermoplasma acidophilum* IFO 15155

*E. coli* HB101 strain transformed with pTG-DSR1 prepared in Example 16 was cultured in 10 mL of 2×YT medium (Tryptone 20 g, Yeast extract 10 g, NaCl 10 g, pH 7.2). After induction, the cells were harvested. The bacterial cells obtained were added to 10 mL of a reaction solution containing 500 mM potassium phosphate (pH 7.5), 5% (309.3 mM) 3-quinuclidinone hydrochloride, and 464.0 mM glucose, and the mixture was incubated at 37° C. overnight while being agitated.

After the bacterial cells were removed, 3-quinuclidinol produced was quantified by the method as described in Example 5. The result showed that the concentration of 3-quinuclidinol hydrochloride was 44.7 g/L and the yield was 88.3%.

The optical purity was determined by the method as descried in Example 5. The result showed that the optical purity was 93.4% ee (R).

EQUIVALENTS

Those skilled in the art will recognize, or be able to ascertain using no more than routine experimentation, many equivalents of the specific embodiments of the invention described herein. Such equivalents are intended to be encompassed by the following claims.

INCORPORATION BY REFERENCE

All patents, pending patent applications and other publications cited herein are hereby incorporated by reference in their entirety.

What is claimed is:

1. A method for producing (R)-3-quinuclidinol hydrochloride having an optical purity of 93.4% ee or higher, the method comprising the steps of:

(a) contacting a 3-quinuclidinone at a concentration of 5 to 50% with an isolated protein selected from the group consisting of the following (i) to (iii) in the presence of a reduced coenzyme to perform asymmetric reduction, a coenzyme-regenerating enzyme which regenerates said reduced coenzyme from its oxidized form, and a substrate for said coenzyme-regenerating enzyme;

(i) an isolated protein comprising the amino acid sequence of SEQ ID NO:2;
(ii) an isolated protein comprising the amino acid sequence of SEQ ID NO:2, wherein one to five amino acids have been substituted, deleted, inserted, and/or added, and having the activity of producing (R)-3-quinuclidinol from 3-quinuclidinone by asymmetric reduction; and
(iii) an isolated protein comprising an amino acid sequence having 95% or higher identity to the amino acid sequence of SEQ ID NO:2, and having the activity of producing (R)-3-quinuclidinol from 3-quinuclidinone by asymmetric reduction;

(b) recovering the (R)-3-quinuclidinol;
(c) adjusting the pH of the (R)-3-quinuclidinol solution to alkaline levels to yield free (R)-3-quinuclidinol;
(d) extracting the free (R)-3-quinuclidinol with n-butanol;
(e) adding hydrochloric acid to the extract;
(f) removing moisture from the extract; and
(g) crystallizing (R)-3-quinuclidinol hydrochloride in the solution obtained in (f).

2. A method for producing (R)-3-quinuclidinol having an optical purity of 93.4% ee or higher, the method comprising the steps of:

(a) contacting a 3-quinuclidinone at a concentration of 5 to 50% with an isolated protein selected from the group consisting of the following (i) to (iii) in the presence of a reduced coenzyme to perform asymmetric reduction, a coenzyme-regenerating enzyme which regenerates said reduced coenzyme from its oxidized form, and a substrate for said coenzyme-regenerating enzyme;
  (i) an isolated protein comprising the amino acid sequence of SEQ ID NO:2;
  (ii) an isolated protein comprising the amino acid sequence of SEQ ID NO:2, wherein one to five amino acids have been substituted, deleted, inserted, and/or added, and having the activity of producing (R)-3-quinuclidinol from 3-quinuclidinone by asymmetric reduction; and
  (iii) an isolated protein comprising an amino acid sequence having 95% or higher identity to the amino acid sequence of SEQ ID NO:2, and having the activity of producing (R)-3-quinuclidinol from 3-quinuclidinone by asymmetric reduction;
(b) recovering the (R)-3-quinuclidinol;
(c) adjusting the pH of the (R)-3-quinuclidinol solution to alkaline levels to yield free (R)-3-quinuclidinol;
(d) extracting the free (R)-3-quinuclidinol with n-butanol;
(e) adding hydrochloric acid to the extract;
(f) removing moisture from the extract;
(g) crystallizing (R)-3-quinuclidinol hydrochloride in the solution obtained in (f);
(h) dissolving (R)-3-quinuclidinol hydrochloride in a first solvent, wherein said first solvent is capable of dissolving (R)-3-quinuclidinol hydrochloride at a concentration of 1% or higher;
(i) adjusting the pH of the solution obtained in (h) to alkaline levels to yield free (R)-3-quinuclidinol;
(j) adding a second solvent to the (R)-3-quinuclidinol solution, wherein said second solvent can substitute for the first solvent by distilling off the first solvent from a mixture of the first and second solvents, dissolving free (R)-3-quinuclidinol with lower solubility than the first solvent, and enabling said free (R)-3-quinuclidinol to crystallize;
(k) distilling off the first solvent; and
(l) crystallizing (R)-3-quinuclidinol in the solution obtained in (k).

3. The method according to claim 2, wherein the second solvent is selected from the group consisting of toluene, hexane, 4-methyl-2-pentanone, and butyl acetate.

4. The method according to claim 2, wherein the first solvent is water, and the second solvent is toluene.

5. The method according to claim 1 or 2, wherein the reduced coenzyme is NADPH or NADH.

6. The method according to claim 1 or 2, wherein the asymmetric reduction is performed in the pH range of 6.5 to 8.5.

7. The method according to claim 1 or 2, wherein the coenzyme-regenerating enzyme is selected from the group consisting of glucose dehydrogenase, glutamate dehydrogenase, formate dehydrogenase, malate dehydrogenase, glucose-6-phosphate dehydrogenase, phosphogluconate dehydrogenase, alcohol dehydrogenase, and glycerol dehydrogenase.

8. The method according to claim 7, wherein the coenzyme-regenerating enzyme is a glucose dehydrogenase.

9. The method according to claim 1 or 2, wherein the substrate for said coenzyme-regenerating enzyme is selected from the group consisting of a sugar, an organic acid, and an alcohol.

10. The method according to claim 9, wherein the substrate for said coenzyme-regenerating enzyme is glucose or sucrose.

\* \* \* \* \*

UNITED STATES PATENT AND TRADEMARK OFFICE
CERTIFICATE OF CORRECTION

| | | |
|---|---|---|
| PATENT NO. | : 7,645,599 B2 | Page 1 of 1 |
| APPLICATION NO. | : 11/151764 | |
| DATED | : January 12, 2010 | |
| INVENTOR(S) | : Yamamoto et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 226 days.

Signed and Sealed this

Sixteenth Day of November, 2010

David J. Kappos
*Director of the United States Patent and Trademark Office*

SEQUENCE LISTING

```
<160> NUMBER OF SEQ ID NOS: 10

<210> SEQ ID NO 1
<211> LENGTH: 822
<212> TYPE: DNA
<213> ORGANISM: Datura stramonium

<400> SEQUENCE: 1
atggaagaat caaaagtgtc catgatgaat tgcaacaatg aaggaagatg gagtctcaaa      60
ggcaccacag cccttgttac tggtggctct aaaggcattg ggtatgcaat agtggaagaa     120
ttggcaggtc ttggagcaag agtatataca tgttcacgta atgaaaaaga actggacgaa     180
tgccttgaaa tttggagaga aaaaggactt aatgttgaag gttctgtttg tgacttatta     240
tcacgtactg aacgtgataa gcttatgcag actgttgcac atgtatttga tggaaagctc     300
aatattttgg tgaataatgc cggggtggtg atacataagg aagctaaaga tttcacagaa     360
aaagattaca acataattat gggaactaat tttgaagcag cttatcattt atctcaaatt     420
gcttatccat tattgaaggc ttctcaaaat gggaatgtta tttttctctc ttctattgct     480
ggattttcag cactgccttc tgtttctctt tactcagctt ccaaaggtgc aataaatcaa     540
atgacaaaga gtttggcttg tgaatgggct aaagacaaca ttcgggtcaa ttcagttgct     600
ccgggagtca ttttaacccc actggttgaa actgcaatta agaaaaatcc tcatcaaaaa     660
gaagaaatag acaattttat tgtcaagact cctatgggcc gggccggaaa gccccaagaa     720
gtttctgcac taatagcttt tctttgcttc cctgctgctt catatattac gggccagatc     780
atatgggctg acggtggatt cacagctaat ggtgggtttt aa                        822

<210> SEQ ID NO 2
<211> LENGTH: 273
<212> TYPE: PRT
<213> ORGANISM: Datura stramonium

<400> SEQUENCE: 2

Met Glu Glu Ser Lys Val Ser Met Met Asn Cys Asn Asn Glu Gly Arg
  1               5                  10                  15

Trp Ser Leu Lys Gly Thr Thr Ala Leu Val Thr Gly Gly Ser Lys Gly
             20                  25                  30

Ile Gly Tyr Ala Ile Val Glu Glu Leu Ala Gly Leu Gly Ala Arg Val
         35                  40                  45

Tyr Thr Cys Ser Arg Asn Glu Lys Glu Leu Asp Glu Cys Leu Glu Ile
     50                  55                  60

Trp Arg Glu Lys Gly Leu Asn Val Glu Gly Ser Val Cys Asp Leu Leu
 65                  70                  75                  80

Ser Arg Thr Glu Arg Asp Lys Leu Met Gln Thr Val Ala His Val Phe
                 85                  90                  95

Asp Gly Lys Leu Asn Ile Leu Val Asn Asn Ala Gly Val Val Ile His
```

```
                        100                 105                 110
Lys Glu Ala Lys Asp Phe Thr Glu Lys Asp Tyr Asn Ile Ile Met Gly
                115                 120                 125

Thr Asn Phe Glu Ala Ala Tyr His Leu Ser Gln Ile Ala Tyr Pro Leu
            130                 135                 140

Leu Lys Ala Ser Gln Asn Gly Asn Val Ile Phe Leu Ser Ser Ile Ala
145                 150                 155                 160

Gly Phe Ser Ala Leu Pro Ser Val Ser Leu Tyr Ser Ala Ser Lys Gly
                165                 170                 175

Ala Ile Asn Gln Met Thr Lys Ser Leu Ala Cys Glu Trp Ala Lys Asp
            180                 185                 190

Asn Ile Arg Val Asn Ser Val Ala Pro Gly Val Ile Leu Thr Pro Leu
        195                 200                 205

Val Glu Thr Ala Ile Lys Lys Asn Pro His Gln Lys Glu Glu Ile Asp
    210                 215                 220

Asn Phe Ile Val Lys Thr Pro Met Gly Arg Ala Gly Lys Pro Gln Glu
225                 230                 235                 240

Val Ser Ala Leu Ile Ala Phe Leu Cys Phe Pro Ala Ala Ser Tyr Ile
                245                 250                 255

Thr Gly Gln Ile Ile Trp Ala Asp Gly Gly Phe Thr Ala Asn Gly Gly
            260                 265                 270

Phe

<210> SEQ ID NO 3
<211> LENGTH: 825
<212> TYPE: DNA
<213> ORGANISM: Hyoscyamus niger

<400> SEQUENCE: 3
atggccggag aatcagaagt ttacattaat ggcaacaatg gaggaattag atggagtctc     60
aaaggcacaa ctgcccttgt tactggtggc tctaaaggca ttgggtatgc agtagtggaa    120
gaactagcag tcttggtgc aagagtatat acatgttcac gtaatgaaaa ggaactccaa    180
caatgccttg atatttggag aaatgaagga cttcaagttg aaggttctgt tgtgattta     240 ttactgcgct ctgaacgtga caaacttatg cagactgttg cagatttatt taatggaaag    300
ctcaatattt tggtaaataa tgcaggtgtg gtgatacata agaagctaa agatttcaca    360 aaagaagatt acgacatcgt attgggcact aattttgaag cagcttatca cttatgtcaa    420
cttgcttatc ccttttgaa ggcatctcaa atggcaatg ttattttct tcttctata      480 gctggatttt cagcactgcc ttctgtttct ctttattctg cttccaaagc tgcaataaat    540
caaataacga gaactggc atgtgaatgg gccaaggaca acattcgggt caattcagtt    600
gctccaggag tcattttaac cccactcatt gaaactgcaa ttaagaaaaa tcctcatcaa    660
aaagaagaaa tagacaattt tattgtcaag actccaatgg gccgggctgg aaagcccaat    720
gaagtgtctg cactaatagc ctttctttgc ttccctgctg cttcttatat tactggccaa    780
attatatggg ctgatggtgg attcacagct aatggtgggt ttga                    825

<210> SEQ ID NO 4
<211> LENGTH: 274
<212> TYPE: PRT
<213> ORGANISM: Hyoscyamus niger

<400> SEQUENCE: 4

Met Ala Gly Glu Ser Glu Val Tyr Ile Asn Gly Asn Asn Gly Gly Ile
```

```
           1               5              10              15

Arg Trp Ser Leu Lys Gly Thr Thr Ala Leu Val Thr Gly Gly Ser Lys
                20                  25                  30

Gly Ile Gly Tyr Ala Val Val Glu Glu Leu Ala Gly Leu Gly Ala Arg
                35                  40                  45

Val Tyr Thr Cys Ser Arg Asn Glu Lys Glu Leu Gln Gln Cys Leu Asp
                50                  55                  60

Ile Trp Arg Asn Glu Gly Leu Gln Val Glu Gly Ser Val Cys Asp Leu
65                  70                  75                  80

Leu Leu Arg Ser Glu Arg Asp Lys Leu Met Gln Thr Val Ala Asp Leu
                85                  90                  95

Phe Asn Gly Lys Leu Asn Ile Leu Val Asn Asn Ala Gly Val Val Ile
                100                 105                 110

His Lys Glu Ala Lys Asp Phe Thr Lys Glu Asp Tyr Asp Ile Val Leu
                115                 120                 125

Gly Thr Asn Phe Glu Ala Ala Tyr His Leu Cys Gln Leu Ala Tyr Pro
        130                 135                 140

Phe Leu Lys Ala Ser Gln Asn Gly Asn Val Ile Phe Leu Ser Ser Ile
145                 150                 155                 160

Ala Gly Phe Ser Ala Leu Pro Ser Val Ser Leu Tyr Ser Ala Ser Lys
                165                 170                 175

Ala Ala Ile Asn Gln Ile Thr Lys Asn Leu Ala Cys Glu Trp Ala Lys
                180                 185                 190

Asp Asn Ile Arg Val Asn Ser Val Ala Pro Gly Val Ile Leu Thr Pro
                195                 200                 205

Leu Ile Glu Thr Ala Ile Lys Lys Asn Pro His Gln Lys Glu Glu Ile
        210                 215                 220

Asp Asn Phe Ile Val Lys Thr Pro Met Gly Arg Ala Gly Lys Pro Asn
225                 230                 235                 240

Glu Val Ser Ala Leu Ile Ala Phe Leu Cys Phe Pro Ala Ala Ser Tyr
                245                 250                 255

Ile Thr Gly Gln Ile Ile Trp Ala Asp Gly Gly Phe Thr Ala Asn Gly
                260                 265                 270

Gly Phe

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 5
ataccatgga agaatcaaaa gtg                                          23

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 6
tggtctagat taaaacccac cattagctgt g                                 31
```

```
<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 7
ataccatggc cggagaatca                                                      20

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 8
acctctagat taaaacccac cattagctgt g                                         31

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 9
caggaattca ataatgactg aacagaaagc cattg                                     35

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 10
ctgactagta ttactgccac tttatcaccg tc                                        32
```